United States Patent [19]
Yedgar et al.

[11] Patent Number: 5,656,501
[45] Date of Patent: Aug. 12, 1997

[54] FLOW CELL DEVICE FOR MONITORING BLOOD OR OTHER CELL SUSPENSION UNDER FLOW

[75] Inventors: Saul Yedgar, Jerusalem; Benjamin Gavish, Mevaseret Zion, both of Israel; Shuqi Chen, Boston, Mass.

[73] Assignee: Yissum Research Development Company of the Hebrew University of Jerusalem, Jerusalem, Israel

[21] Appl. No.: 466,026

[22] Filed: Jun. 6, 1995

Related U.S. Application Data

[63] Continuation of Ser. No. 191,507, Feb. 4, 1994, abandoned.

[30] Foreign Application Priority Data

Aug. 11, 1993 [IL] Israel .................................. 106662

[51] Int. Cl.$^6$ ........................... G01N 33/49; G01N 21/05
[52] U.S. Cl. ........................... 436/63; 436/70; 436/174; 436/180; 422/73; 422/100; 356/39; 356/244; 356/246
[58] Field of Search ........................... 436/63, 69, 174, 436/70, 180, 183, 807; 422/55, 58, 73, 99, 100, 104; 435/291; 356/39, 244, 246

[56] References Cited

U.S. PATENT DOCUMENTS

| | | | |
|---|---|---|---|
| 2,656,508 | 10/1953 | Coulter | 324/71.1 |
| 3,612,281 | 10/1971 | Leonard | 210/321 |
| 3,839,204 | 10/1974 | Ingenito et al. | 210/181 |
| 3,916,205 | 10/1975 | Kleinerman | 250/461 |
| 4,135,819 | 1/1979 | Schmid-Schönbein | 356/39 |
| 4,338,024 | 7/1982 | Bolz et al. | 356/23 |
| 4,627,419 | 12/1986 | Hills | 128/1 D |
| 4,734,372 | 3/1988 | Rotman | 435/291 |
| 4,765,899 | 8/1988 | Wells et al. | 210/519 |
| 4,822,568 | 4/1989 | Tomita | 422/73 |
| 4,976,861 | 12/1990 | Pall | 210/508 |
| 5,089,421 | 2/1992 | Dieffenbach | 436/68 |
| 5,207,988 | 5/1993 | Lucas | 422/73 |
| 5,278,048 | 1/1994 | Parce et al. | 436/29 |
| 5,300,779 | 4/1994 | Hillman et al. | 250/341 |
| 5,316,730 | 5/1994 | Blake et al. | 422/73 |

*Primary Examiner*—Long V. Le
*Attorney, Agent, or Firm*—Lowe, Price, LeBlanc & Becker

[57] ABSTRACT

A flow cell for monitoring blood or any other cell suspension under flow comprises a rigid transparent base having a pair of holes with inlets and outlets. One hole transfers the cell suspension from a supply to a flow channel and the other hole transfers the tested suspension back from the flow channel to a receiver. A flow plate is sandwiched between the base and a transparent plate. The flow channel is a wide hole in the middle of the flow channel plate which can be an integral part of either the base or the transparent plate. The transparent plate covers the flow channel plate and a rigid cover covers the transparent plate with a hole enabling a microscope objective to approach the flow channel plate. The transparent plate and the cover are attached to each other firmly by any conventional method or the transparent plate can be an integral part of the cover.

19 Claims, 4 Drawing Sheets

FLOW CELL DEVICE FOR MONITORING BLOOD OR OTHER CELL SUSPENSION UNDER FLOW

This application is a continuation of Application Ser. No. 08/191,507 filed Feb. 4, 1994, now abandoned.

FIELD OF THE INVENTION

This invention relates to a flow cell device for the monitoring of blood or any other cell suspension under flow. More specifically, the object of the present invention is to easily monitor the other cell—particularly red blood cells—and their dynamic organization under flow conditions, as well as their shape and deformability, using small samples of suspensions, with a safe and cost effective procedure. The flow of blood or other cells suspension in the abovementioned flow cell is visualized through a microscope. The supplying and receiving of the suspension sample to and from the flow cell is by means of syringes or any other appropriate device. This invention may be used in a system connected to a video camera, computer and image monitor (Computerized image analyzer system).

BACKGROUND OF THE INVENTION

Red blood cells at rest (stasis) forms aggregates, which are disaggregated gradually with increasing blood flow. The degree of aggregation and the aggregate structure reflect a delicate balance between chemical and hydrodynamic forces. In stasis, when flow forces are absent, the interaction between the cell membrane and plasma proteins will cause the red cells to aggregate into stacks called rouleaux, which further interact to form networks. Cell aggregation is a reversible process and the blood therefore follows dynamic changes according to flow conditions. The aggregability of red blood cells (hereinafter called RBC), which is a major determinant in blood circulation, strongly depends on the cells physical and chemical properties, and is very sensitive to changes in these properties. The size and number of red blood cell aggregates dominate the blood viscosity which plays a central role in blood flow in vessels of constant diameter. Thus the blood flow to tissues is largely affected by the aggregability of the RBC. The tendency of RBCs to form aggregates and thrombi under flow is a structural property of dynamic origin which is closely associated with the risk of diminished blood supply and the plugging of small blood vessels, pathologies which are important factors in stroke, shock, and damage caused to organs by various vascular diseases. The aggregation and disaggregation of RBC play a central role in blood flow, especially in microvessels and in states of lowered blood flow. Increased RBC aggregability occurs in many disease states (e.g. coronary heart diseases, diabetes, hyperviscosity syndrome, thrombosis, trauma and sickle cell anemia), and is considered to be a risk factor. Recent application of video microscopes enables a glimpse into this complicated type of flow. However, quantitative information about RBC organization under flow is still minimal, in spite of its great clinical significance.

Another important property of cells, particularly of blood cells, is their deformability, i.e. their ability to change shape and thus to pass through small blood vessels. Variations in the blood cells deformability contribute to various cardiovascular and microcirculatory disorders.

The present invention enables the visualization of RBC in a flow cell and analysis of the aggregability size and deformability under varying flow conditions. The depth of the flow cell is such that it enables a single layer of aggregates to pass through the cell, and provides a two dimensional array of the structures. The form of the cross section and the flow channel is important for generating flow gradients which are the origin of these disaggregating forces. This invention therefore is a novel and powerful tool for real-time monitoring of cell-to-cell interaction which is altered in pathological states and affected by drugs. This system enables study of the dynamic organization of cell suspensions; including flow related properties of such cells, such as cell deformability and shape, as well as the interaction between a cell or aggregate with the blood vessel wall, thus adding a new dimension to existing blood tests, and enriching the knowledge of blood rheology (the science of blood flow).

The creation of a flowing two dimensional aggregate layer requires a narrow gap. This imposes a practical problem of cleaning the flow cell and the tubing after each test. The problem becomes severe in the case of automatic testing in a commercial product that should withstand safety regulations.

SUMMARY OF THE INVENTION

The present invention relates to a disposable flow cell device for the monitoring of the behavior of blood or any other cells suspension under flow, particularly suspensions of red blood cell. The above mentioned flow cell is comprised of a rigid transparent base, having a pair of holes is used with inlets and outlets. One hole for transferring the blood from a supplying means to a flow channel, and the other hole is used for transferring the tested blood back from the flow channel to a receiving means. However, the role of the "supplier" and the "receiver" could be changed intermittently. The flow channel plate is located between the base and a transparent plate covering the flow channel plate, wherein the flow channel is a wide hole (of varying shape and size) in the middle of the flow channel plate. A rigid cover covers the transparent plate, with a hole enabling a microscope objective to approach the flow channel plate. The base, flow channel plate, transparent plate and cover of the flow cell may be attached to each other by glue or screws, or the flow channel plate may be an integral part of either the base or the transparent plate in one piece, or the cover, the transparent base and flow channel plate can all be one piece. The method of supplying and receiving the suspension sample to and from the flow cell is by means of syringes, flexible caps, bellow, or any other appropriate device, inserted into the inlet and outlet of the base respectively. The above mentioned flow cell may be used in a system in which a video camera is mechanically connected to the microscope, and a computer and an image monitor connected to each other can be connected to the microscope.

DETAILED DESCRIPTION OF THE INVENTION

Figure 1:
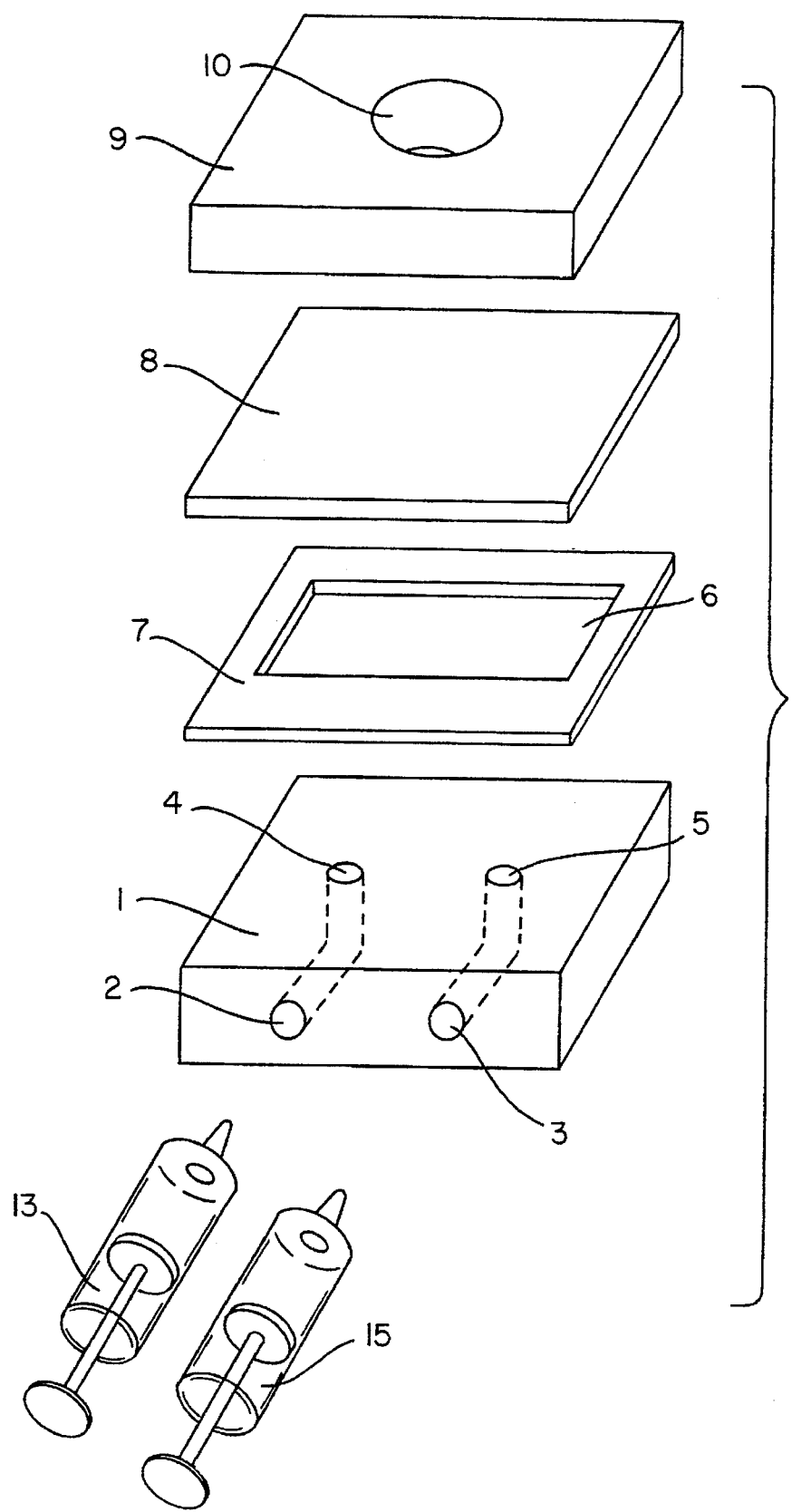
FIG. 1 illustrates an isometric view of the seperate components of the flow cell.

The flow cell device according to the present invention illustrated in FIG. 1, comprises a rigid transparent base (1) which contains an inlet (2) and an outlet (3) for transferring the cell suspension to the actual flow channel (6) through openings (4) and (5). These holes also form reservoirs for the tested sample. The flow channel (6) is formed by a hole in the channel flow plate (7) which is sandwiched between the base (1) below and a transparent plate (8) above. A rigid cover (9) with a hole (10) enables the microscope objective to approach the flow channel (6). The rigidity of the cover (9) and the base (1) assure that the flow channel depth will not be affected by the pressure applied. The base (1) flow channel plate (7), transparent plate (8) and cover (9) can be attached to each other firmly by using bond, screws or by other methods, or the the flow channel plate (7) can be an integral part (one piece) of either the base (1) or the transparent plate (8), or the the cover (9), the transparent plate (8) and the flow channel plate (7) can be one piece, attached to the other parts by methods to be decided upon following engineering considerations. The preferred embodiment of this invention comprises a rectangular flow channel having a depth of 20–40 microns (comparable to the diameter of arterial microvessels—enough to enable the flow of aggregates but thin enough to produce a two dimensional layer of such aggregates.)

Figure 2A:
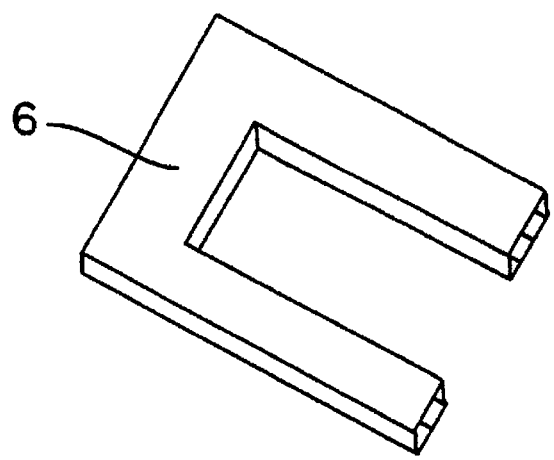
FIGS. 2(a), 2(b) and 2(c) illustrate flow channels of different types.
Figure 2B:
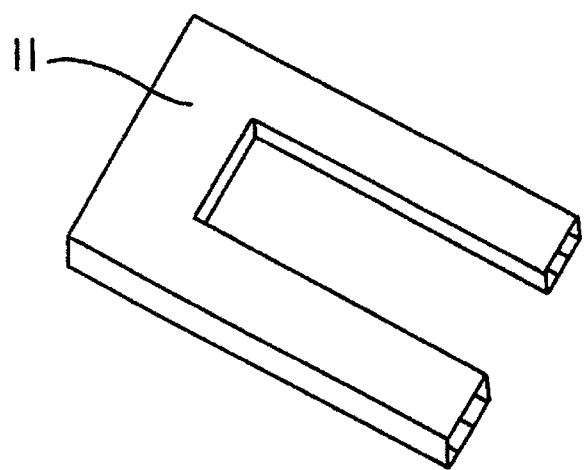
Figure 2C:
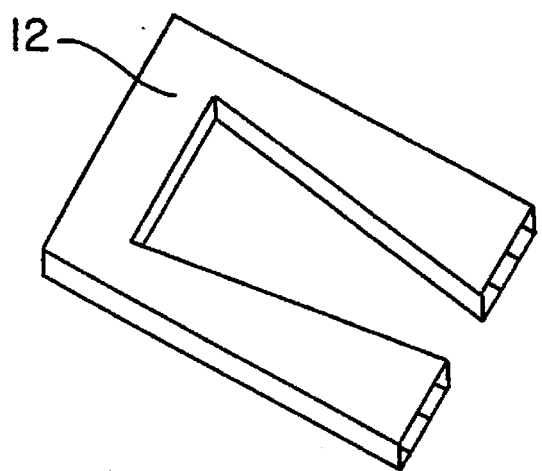

FIG. 2 describes possible shapes of the flow channel: Different types of flow can be produced by giving the flow channel a non-constant width (11) (speed varies along the channel), or by using a flow channel with a trapezoidal cross section (12), which leads to a flow with velocity gradients vertically to the flow direction. These flow patterns are important and known to occur in vivo.

Figure 3:
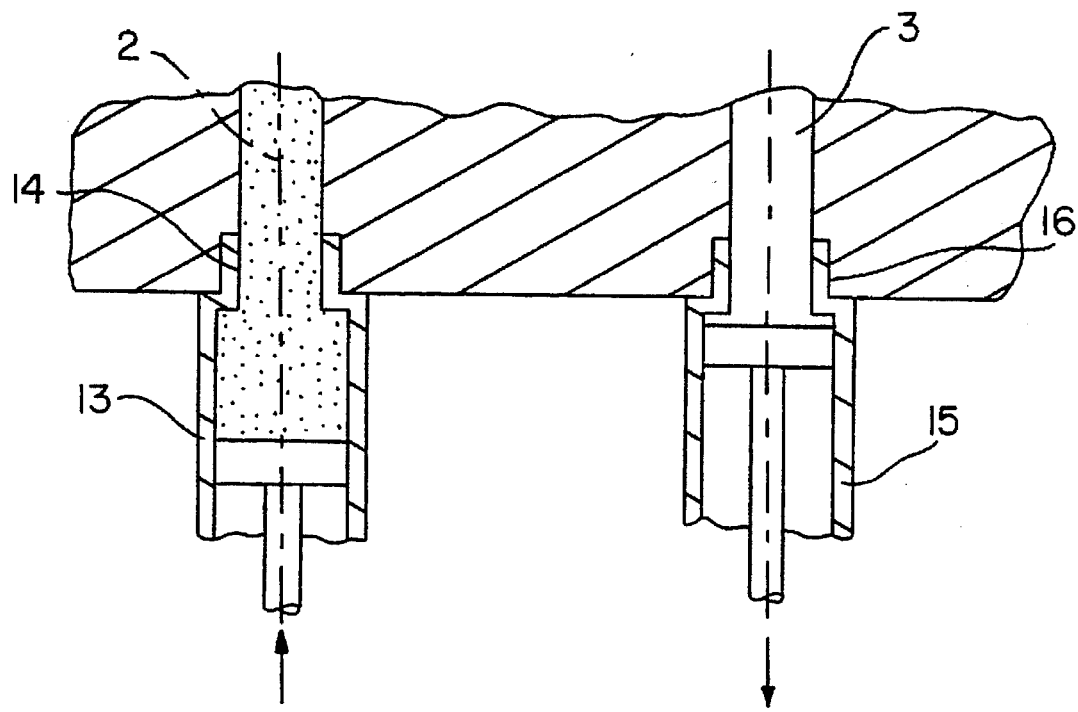
FIG. 3 illustrates a cross section of the supplying syringe and the receiving syringe

FIG. 3 represents a cross section of the supplying and receiving means. The supplying syringe (13) (which is used to take the sample) is fixed firmly inside the inlet hole (2), at its conic opening (14). An initially empty (15) syringe is attached to the outlet hole (3) at a similar opening (16). The invention is used by the following method: After syringe (13) is attached to the flow cell, the piston of the "inlet" syringe (13) is pushed, while that of the "outlet" syringe is pulled with the same force by a simple mechanical arrangement, which is not part of the patent application. After the reservoir (4) is filled with the cell suspension a flow can be developed in a repeatable way by switching between the pushing and pulling operation. By controlling the piston velocity the flow can be controlled. All the filling procedure and flow control can be done automatically.

Figure 4:
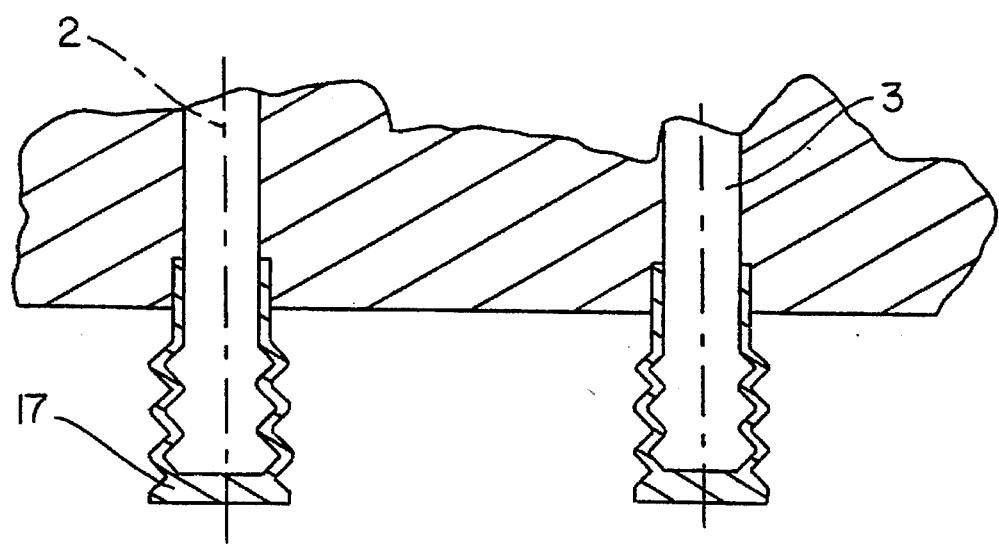
FIG. 4 illustrates a cross section of a bellows as (an alternative supplying and receiving means) inserted in the inlet and outlet of the rigid base.

FIG. 4 demonstrates alternatives to the syringes (13,15). A flexible cap or bellows (17) could be used which could change the cell volume with minimal pressure and enable injection of blood through the top using a needle while keeping the cell leak proof.

Figure 5:
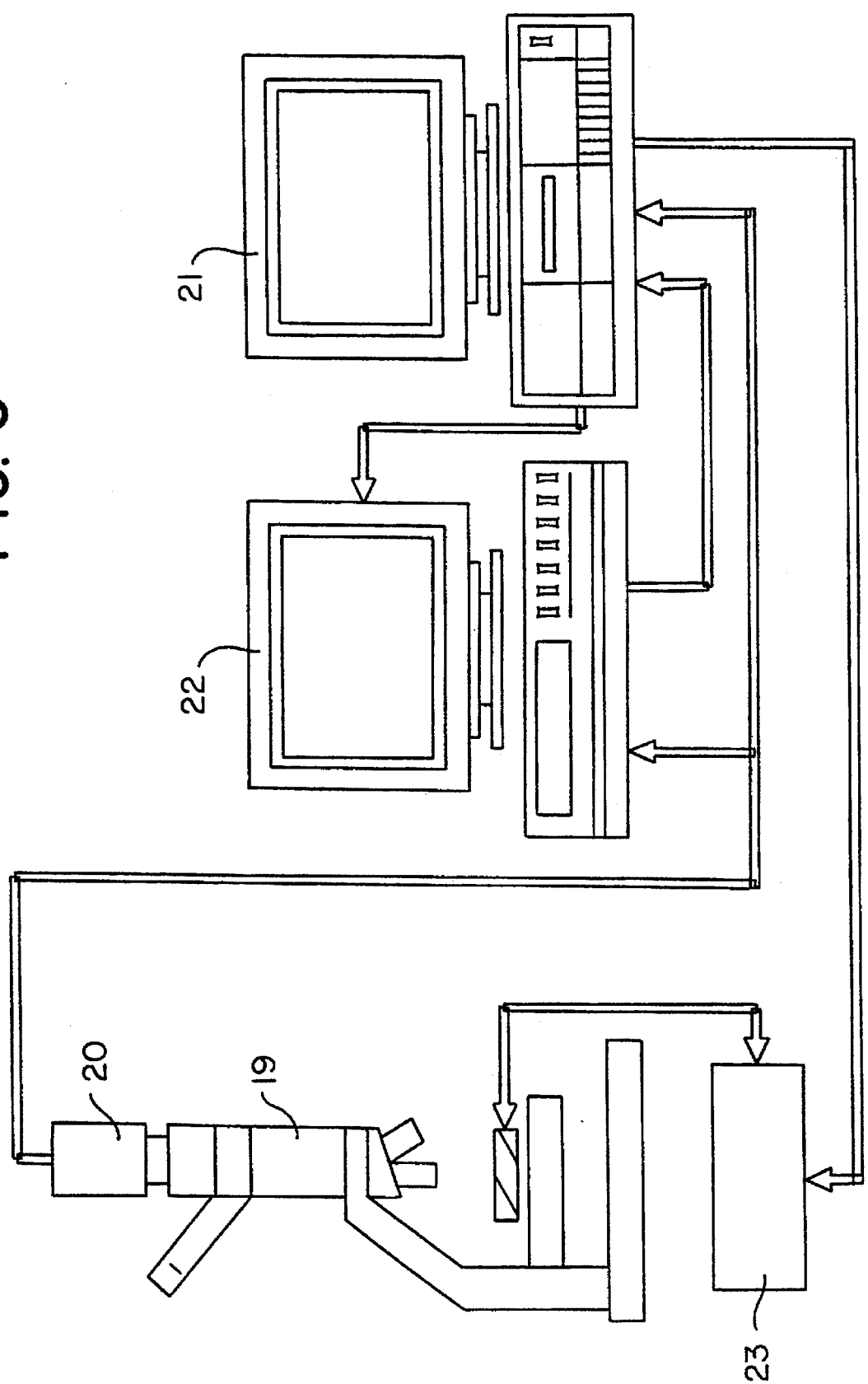
FIG. 5 shows a schematic diagram of a computerized image analyzer system using the flow cell according to this invention.

FIG. 5 illustrates a system in which the present invention can be used. The microscope (19) approaching the flow cell is mechanically connected to a video camera (20), connected to a computer (21) and image analyzer (22). A pump (23) can be connected to the computer as another alternative supplying and receiving means.

We claim:

1. A flow cell device for monitoring blood or a cell suspension under flow, comprising: a rigid transparent base having a pair of holes; a transparent plate and a flow channel plate of a constant thickness sandwiched between the base and the transparent plate to define a flow channel of a constant depth in the form of a hole in a center portion of the flow channel plate, said flow channel depth allowing the flow of only a single layer of blood or cell suspension aggregates; wherein each of said pair of holes is formed with an inlet and outlet, one said hole for transferring the cell suspension from a supply to the flow channel and the other hole for transferring said blood or suspension back from the flow channel to a receiver; and a rigid cover covering the transparent plate and being formed with a hole enabling a microscope objective to approach the flow channel plate.

2. A flow cell device according to claim 1, wherein the flow cell is disposable.

3. A flow cell device according to claim 1, wherein the flow channel has a depth to enable detection of aggregation and disaggregation, cell deformability and shape, and cell-wall, cell-to-cell, and cell-to-extracellular-matrix interaction of blood and cell suspension.

4. A flow cell device according to claim 1, wherein a thickness of the flow channel plate is 20–40 microns to establish said flow channel depth.

5. A flow cell device according to claim 1 wherein the flow channel plate has a constant depth.

6. A flow cell device according to claim 1 wherein the flow channel plate has a constant cross section.

7. A flow cell device according to claim 3 wherein the flow channel plate has a variable width.

8. A flow cell device according to claim 1 wherein the flow channel plate has a polygonal cross-section.

9. A flow cell device according to claim 1 wherein the flow channel plate has a variable cross-section.

10. A flow cell device according to claim 7 wherein the flow channel plate hole has a rectangular or trapezoidal cross-section.

11. A flow cell device according to claim 1 wherein the base, the flow channel plate, the transparent plate and the cover are attached to each other by at least one of glue and screws.

12. A flow cell device according to claim 1 wherein said supply and receiver are at least one of syringes and flexible caps.

13. The flow cell device of claim 1, wherein said flow channel plate is of integral construction with the base.

14. The flow cell device of claim 1, wherein said flow channel plate is of integral construction with the transparent plate.

15. The flow cell device of claim 1, wherein said transparent plate is of integral construction with the cover.

16. A method for monitoring the behavior of cell suspensions under flow using a flow cell including a flow cell device for monitoring blood or a cell suspension under flow, comprising a rigid transparent base having a pair of holes, a transparent plate and a flow channel plate of a constant thickness sandwiched between the base and the transparent plate to define a flow channel of a constant depth in the form of a hole in a center portion of the flow channel plate, said flow channel depth allowing the flow of only a single layer of blood or cell suspension aggregates, wherein each of said pair of holes is formed with an inlet and outlet, one said hole for transferring the cell suspension from a supply to the flow channel and the other hole for transferring said blood or suspension back from the flow channel to receiver, and a rigid cover covering the transparent plate and being formed with a hole enabling a microscope objective to approach the flow channel plate, comprising the steps of:

(a) fixing a syringe with a cell suspension to be tested to the inlet hole of the rigid transparent base;

(b) fixing an empty syringe to the outlet hole of the said base; and (c) pushing the piston of the syringe with the cell suspension and simultaneously pulling the piston of the empty syringe to move the single layer of blood or cell suspension aggregates back and forth through the flow channel.

17. A method according to claim 16, comprising the further steps of repeatedly reversing the roles of the receiver and supply to enable prolonged detection of the cell suspension under flow.

18. A method according to claim 16 wherein said syringes are flexible caps.

19. A computerized image analyzer system for detection and visualization of suspension cells under flow, comprising:

a flow cell device including a rigid transparent base having a pair of holes, a transparent plate, a flow channel plate of a constant thickness sandwiched between the base and the transparent plate to define a flow channel of a constant depth in the form of a hole in a center portion of the flow channel plate, and a rigid cover covering the transparent plate and being formed with a hole, said flow channel depth allowing the flow of only a single layer of blood or cell suspension aggregates, each of said pair of holes being formed with an inlet and outlet, one said hole for transferring the cell suspension from a supply to the flow channel and the other hole for transferring said blood or suspension back from the flow channel to a receiver;

a microscope being movably mounted to approach the flow channel through the cover hole;

a video camera mechanically connected to said microscope;

a computer and an image monitor both connected to each other and to the video camera; and a pump force or generator that operates said supply or receiver, and being connected to the computer and to the flow cell device to direct the suspension back and forth in the flow cell device.

* * * * *